(12) United States Patent
Mirosevich

(10) Patent No.: US 8,921,111 B2
(45) Date of Patent: Dec. 30, 2014

(54) POLYMER BASED POLYNUCLEOTIDE TRANSFECTION AGENTS

(71) Applicant: Intezyne Technologies, Inc., Tampa, FL (US)

(72) Inventor: Janni Mirosevich, Tampa, FL (US)

(73) Assignee: Intezyne Technologies, Tampa, FL (US)

( * ) Notice: Subject to any disclaimer, the term of this patent is extended or adjusted under 35 U.S.C. 154(b) by 0 days.

(21) Appl. No.: 14/164,845

(22) Filed: Jan. 27, 2014

(65) Prior Publication Data

US 2014/0302607 A1 Oct. 9, 2014

Related U.S. Application Data

(60) Provisional application No. 61/756,863, filed on Apr. 8, 2013.

(51) Int. Cl.
*C12N 15/88* (2006.01)

(52) U.S. Cl.
CPC ...................... *C12N 15/88* (2013.01)
USPC ......................... 435/455; 435/375

(58) Field of Classification Search
CPC ....................................... C12N 15/88
USPC ........................................... 435/455
See application file for complete search history.

(56) References Cited

U.S. PATENT DOCUMENTS

| 2008/0112916 A1 | 5/2008 | Wagner et al. | |
| 2010/0278927 A1 | 11/2010 | Mirosevich et al. | |
| 2010/0292432 A1 | 11/2010 | Cardoen et al. | |
| 2011/0229528 A1* | 9/2011 | Mirosevich et al. | .......... 424/400 |
| 2012/0148631 A1* | 6/2012 | Mirosevich et al. | .......... 424/400 |

OTHER PUBLICATIONS

Wolfert, Margreet A., et al., Characterization of Vectors for Gene Therapy Formed by Self-Assembly of DNA with Synthetic Block Co-Polymers, Human Gene Therapy, vol. 7, pp. 2123-2133 (1996).
Itaka, Keiji, et al., Biodegradable Polyamino Acid-Based Polycations as Safe and Effective Gene Carrier Minimizing Cumulative Toxicity, Biomaterials, 8 pgs. (2010).
Kataoka, Kazunori, et al., Block Copolymer Micelles for Drug Delivery: Design, Characterization and Biological Significance, Advanced Drug Delivery Reviews, vol. 47, pp. 113-131 (2001).
Han, Muri, et al., Transfection Study Using Multicellular Tumor Spheroids for Screening Non-Viral Polymeric Gene Vectors with Low Cytotoxicity and High Transfection Efficiencies, Journal of Controlled Release, vol. 121, pp. 38-48 (2007).
Tagami, Tatsuaki, et al., The Gene-Silencing Effect of siRNA in Cationic Lipoplexes is Enhanced by Incorporating pDNA in the Complex, International Journal of Pharmaceutics, vol. 333, pp. 62-69 (2007).
Miyata, Kanjiro, et al., Polyplexes from Poly(aspartamide) Bearing 1,2-Diaminoethane Side Chains Induced pH-Selective, Endosomal Membrane Destabilization with Amplified Transfection and Negligible Cytotoxicity, J. Am. Chem. Soc., vol. 130, pp. 16287-16294 (2008).

* cited by examiner

*Primary Examiner* — Scott Long
(74) *Attorney, Agent, or Firm* — Kevin Sill

(57) ABSTRACT

The present invention provides a methodology for transfecting cells in vitro. In particular, cationic polymers and polynucleotide containing polyplexes comprising such polymers are provided.

2 Claims, 4 Drawing Sheets

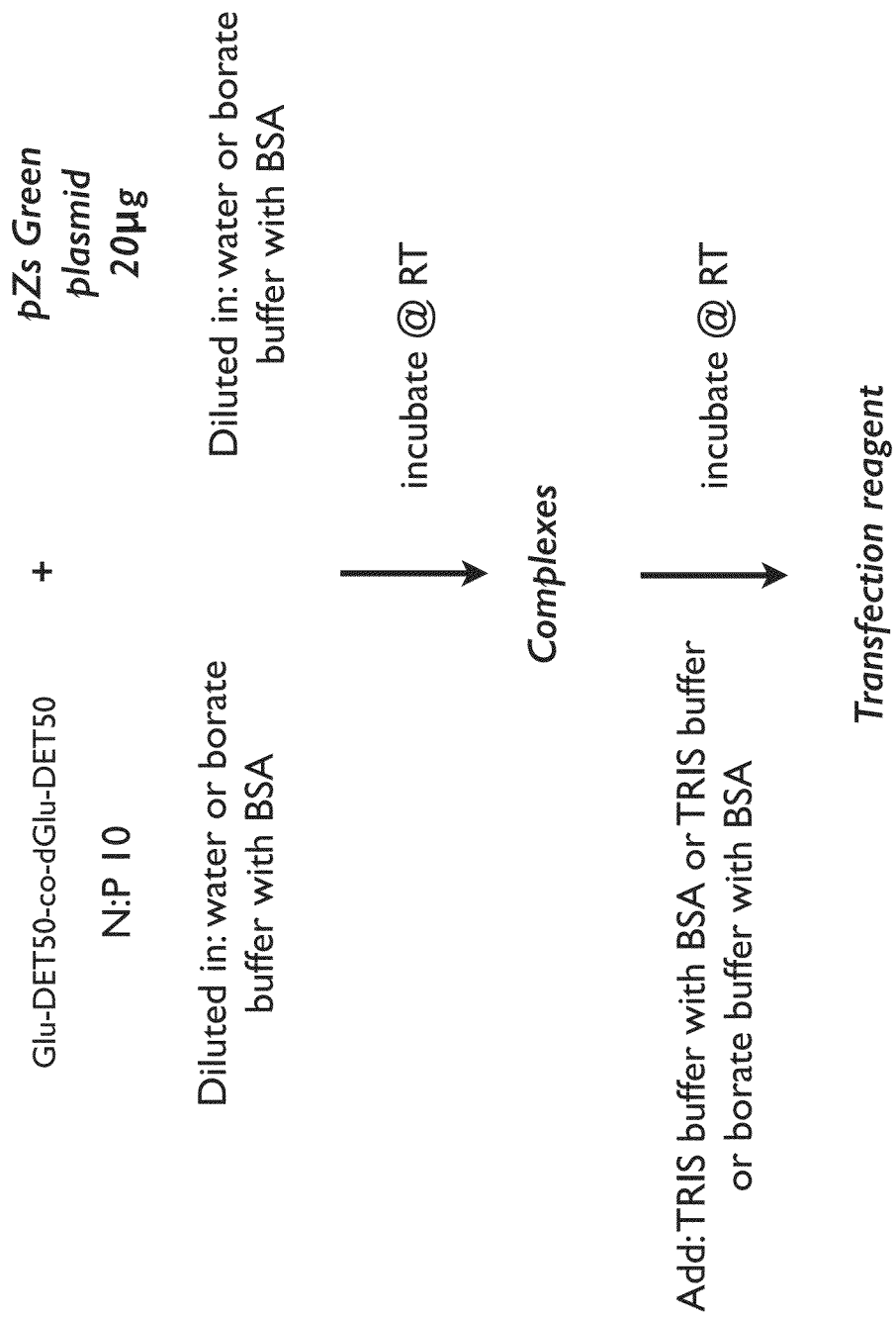

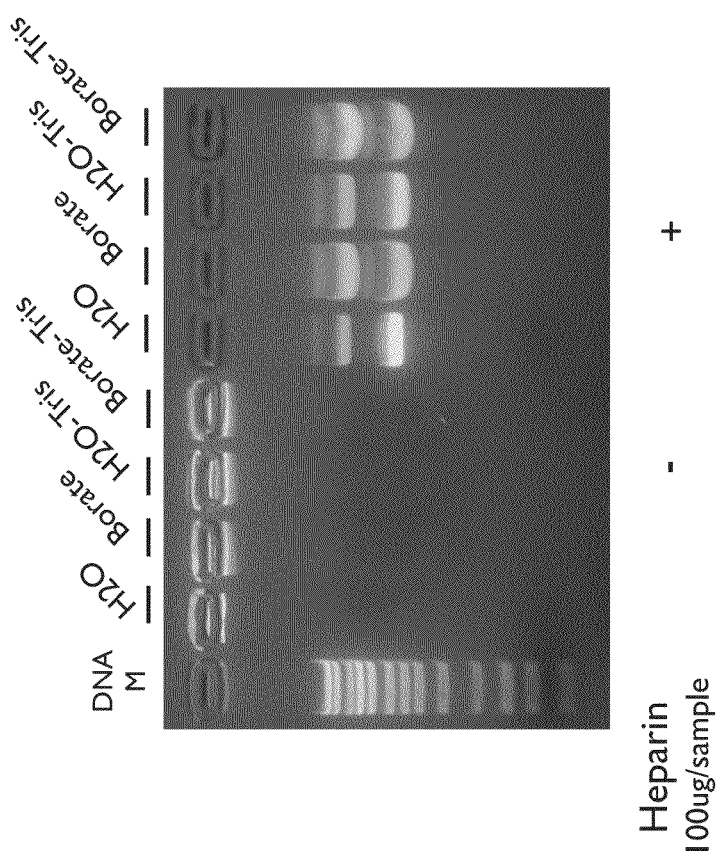
Figure 2: Gel Retardation of DNA Complexed with D/L Glu-DET in Different Buffer Conditions

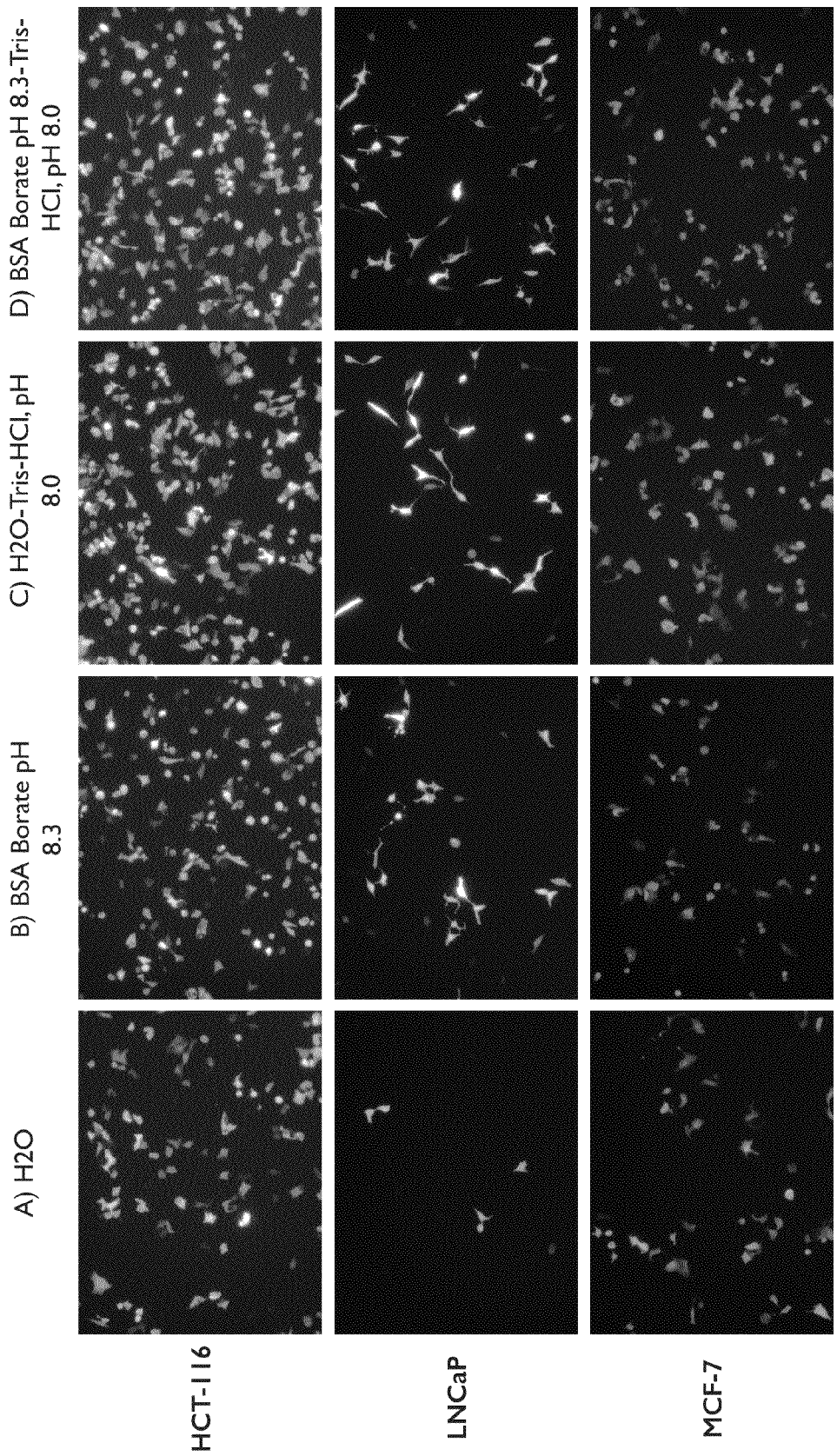

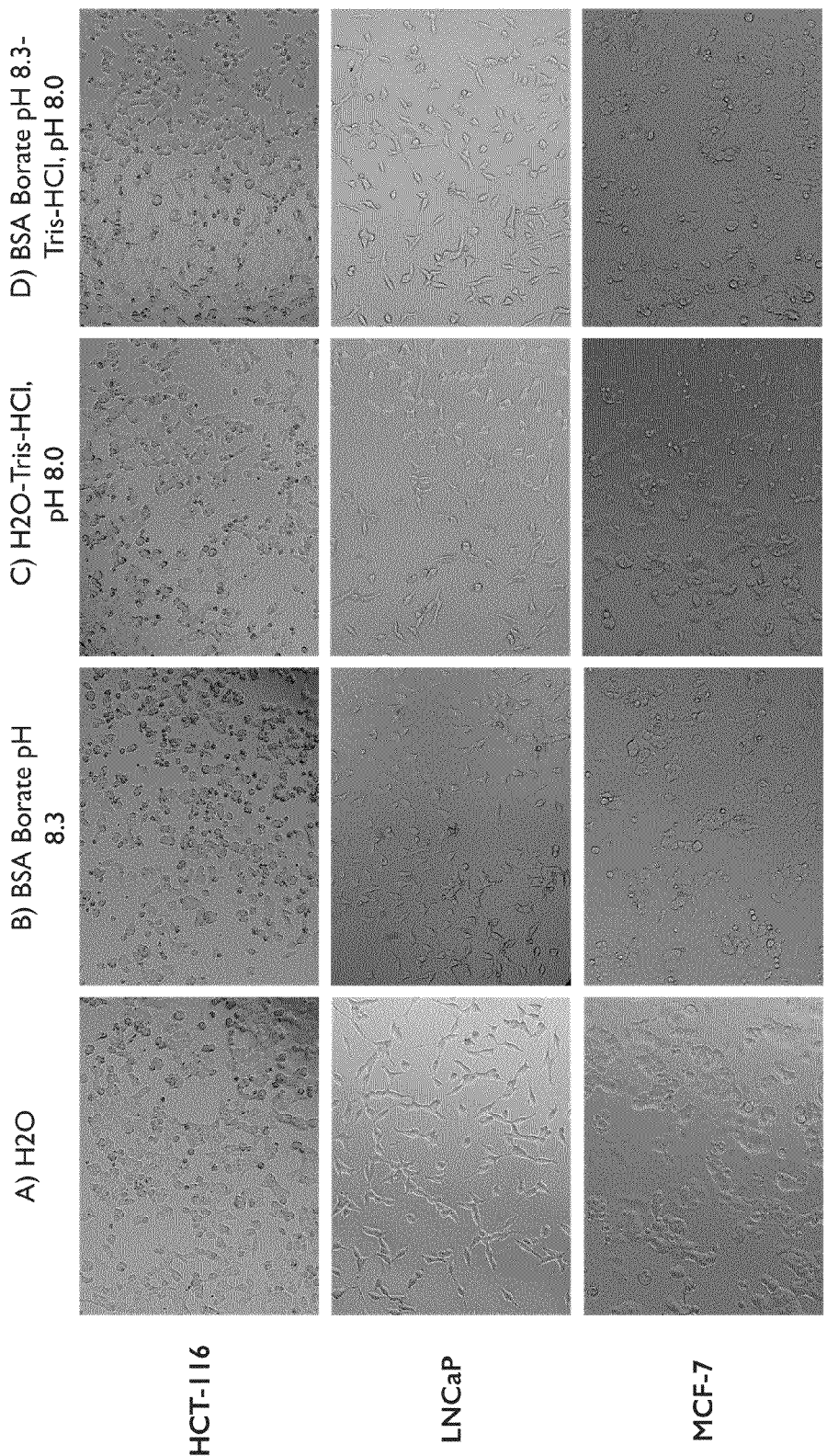

POLYMER BASED POLYNUCLEOTIDE TRANSFECTION AGENTS

CROSS REFERENCE TO RELATED APPLICATIONS

The present application claims priority to U.S. provisional patent application Ser. No. 61/756,863, filed Jan. 25, 2013, the entirety of which is hereby incorporated by reference herein.

FIELD OF THE INVENTION

The present invention relates to the field of polymer chemistry and more particularly to the formation of polynucleotide containing polyplexes and uses thereof.

BACKGROUND OF THE INVENTION

Understanding the role of altered gene expression in the development and progression of diseases such as cancer is a major focus of today's research. To determine a gene's function, researchers frequently perform transfection experiments to introduce or remove genes to cells grown in culture. Currently, the most common non-viral transfection methods used in the laboratory include cationic polymers, liposomes and denrimers. All these systems have positive charges that interact with nucleic acids to form complexes which can be internalized by cells. Currently, these non-viral methods are limited in terms of low transfection efficiency and high cell toxicity. Further, transfection protocols are typically laborious and require numerous steps to perform. Here we describe the development of new polycation/nucleic acid formulations for cell transfection. These new transfection reagents are simple to formulate, produce reproducible results, transfect numerous cell lines with high efficiency and display low cell toxicity.

BRIEF DESCRIPTION OF THE DRAWINGS

FIG. 1. Schematic representation of polyplex formation.
FIG. 2. Gel retardation study of DNA complexed with D/L Glu-DET polymers.
FIG. 3. GFP expression of cancer cells transfected with D/L Glu-DET polymers.
FIG. 4. Cell viability of cancer cells transfected with D/L Glu-DET polymers.

DETAILED DESCRIPTION OF CERTAIN EMBODIMENTS OF THE INVENTION

1. General Description

In vitro cell transfection experiments are commonly used in molecular biology to determine how altered gene expression affects cell proliferation, differentiation and apoptosis. Transfection involves the introduction of exogenous genetic material, via viral and non-viral methods, into cells. Non-viral transfection methods are commonly used in laboratories that investigate the role of genes in the development and progression of diseases such as cancer. These non-viral transfection methods incorporate either polymer, liposomal or denrimer components that are positively charged and can interact with nucleic acids to form particles that are capable of cell internalization, have endosome escape properties and can subsequently transport genetic payloads to either the nucleus or cytoplasm. However, all of these non-viral approaches suffer from limited cell compatibility, low transfection efficiencies or cytotoxicity effects on the cells being transfected. Therefore, developing a transfection reagent/procedure that is reproducible, transfects efficiently with low cell toxicity will prove most beneficial.

The overall size of the transfection complexes is known to be an important factor for efficient cell internalization and high transfection efficiency. Two other aspects of a transfection system must also be considered; the buffering capacity of the polycation and the intracellular release of the polynucleotide from the cationic polymer.

The present invention describes the preparation of a buffered polycation polymer/nucleic acid formulation for the transfection of cells grown in culture. This transfection formulation method can be applied to both DNA and siRNA, and offers reproducibility, high transfection efficiency and low toxicity in numerous cell lines. In certain aspects, the present invention provides a polycation which is comprised of a poly (amino acid) (PAA) backbone with amine containing side chain groups.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "portion" or "block" refers to a repeating polymeric sequence of defined composition. A portion or a block may consist of a single monomer or may be comprise of on or more monomers, resulting in a "mixed block".

One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by $[(A)_4(B)_4(C)_4(D)_4]$.

As used herein, the term "polycation" or "cationic polymer" may be used interchangeably and refer to a polymer possessing a plurality of ionic charges. In some embodiments polycation also refers to a polymer that possess a plurality of functional groups that can be protonated to obtain a plurality of ionic charges. For clarity, a polymer that contains a plurality of amine functional groups will be referred to as a polycation or a cationic polymer within this application.

In certain embodiments, a provided cation is suitable for polynucleotide encapsulation. As used herein, the term "polynucleotide" refers to DNA or RNA. In some embodiments, a polynucleotide is a short interfering RNA (siRNA), a microRNA (miRNA), a plasmid DNA (pDNA), a short hairpin RNA (shRNA), messenger RNA (mRNA), antisense RNA (asRNA), to name a few, and encompasses both the nucleotide sequence and any structural embodiments thereof, such as double stranded, single stranded, helical, hairpin, etc.

As used herein, the terms "polynucleotide-loaded" and "encapsulated," and derivatives thereof, are used interchangeably. In accordance with the present invention, a "polynucleotide-loaded" polyplex refers to a polyplex having one or more polynucleotides situated within the core of the polyplex. This is also referred to as a polynucleotide being "encapsulated" within the polyplex.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit is in the L-configuration. In other embodiments, the amino acid units are a mixture of D and L configurations. Such poly(amino acids) include those having suitably protected functional groups. For example, amino acid monomers may have hydroxyl or amino moieties that are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In still other embodiments, amino acid blocks of the present invention include random amino acid blocks, i.e., blocks comprising a mixture of amino acid residues.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the term "D,L-mixed poly(amino acid)" refers to a poly(amino acid) wherein the poly(amino acid) consists of a mixture of amino acids in both the D- and L-configurations. It is well established that homopolymers and copolymers of amino acids, consisting of a single stereoisomer, may exhibit secondary structures such as the α-helix or β-sheet. See α-Aminoacid-N-Caroboxy-Anhydrides and Related Heterocycles, H. R. Kricheldorf, Springer-Verlag, 1987. For example, poly(L-benzyl glutamate) typically exhibits an α-helical conformation; however this secondary structure can be disrupted by a change of solvent or temperature (see *Advances in Protein Chemistry XVI,* P. Urnes and P. Doty, Academic Press, New York 1961). The secondary structure can also be disrupted by the incorporation of structurally dissimilar amino acids such as β-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

As used herein, the term "tacticity" refers to the stereochemistry of the poly(amino acid). A poly(amino acid) block consisting of a single stereoisomer (e.g. all L isomer) is referred to as "isotactic". A poly(amino acid) consisting of a random incorporation of D and L amino acid monomers is referred to as an "atactic" polymer. A poly(amino acid) with alternating stereochemistry (e.g. ... DLDLDL ... ) is referred to as a "syndiotactic" polymer. Polymer tacticity is described in more detail in "Principles of Polymerization", 3rd Ed., G. Odian, John Wiley & Sons, New York: 1991, the entire contents of which are hereby incorporated by reference.

As used herein, the phrase "unnatural amino acid side-chain group" refers to the side-chain group of amino acids not included in the list of 20 amino acids naturally occurring in proteins, as described above. Such amino acids include the D-isomer of any of the 20 naturally occurring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As used herein, the phrase "amine-containing amino acid side-chain group" refers to natural or unnatural amino acid side-chain groups, as defined above, which comprise an amine moiety. The amine moiety may be primary, secondary, tertiary, or quaternary, and may be part of an optionally substituted group aliphatic or optionally substituted aryl group.

As used herein, the phrase N to P (N/P or N:P) refers to the ratio of protonatable nitrogens (N) to negatively charged phosphate groups in the DNA or RNA backbone (P).

The term "aliphatic" or "aliphatic group," as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4- dihydro-2H-pyrrolyl, —NH— as in pyrrolidinyl, or =N(R+)— as in N-substituted pyrrolidinyl.

The term "unsaturated," as used herein, means that a moiety has one or more units of unsaturation.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring."

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, in neutron scattering experiments, as analytical tools, or probes in biological assays.

The terms "fluorescent label," "fluorescent group," "fluorescent compound," "fluorescent dye," and "fluorophore," as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "substrate," as used herein refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (eg., latex, polystyrene, or other polymer), porous polymer matrices (e.g., polyacrylamide gel, polysaccharide, polymethacrylate), macromolecular complexes (e.g., protein, polysaccharide).

3. Description of Exemplary Embodiments:

A. Cationic Polymers

The preparation and use of the polymers described herein has been previously presented in U.S. patent application US20110142886, which is hereby incorporated as reference.

In certain embodiments, the present invention provides a cationic polymer of formula I, or a salt thereof:

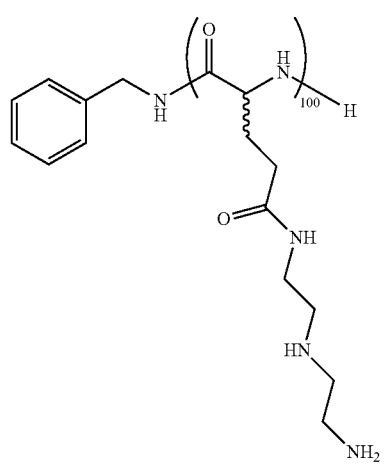

I

In certain embodiments, the present invention provides a cationic polymer of formula II, or a salt thereof:

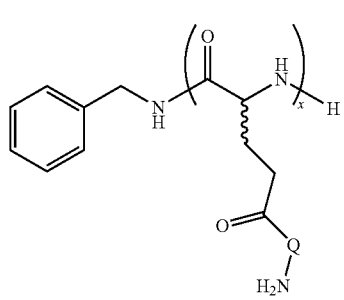

II wherein:
x is 10-250; and
Q is a valence bond or a bivalent, saturated or unsaturated, straight or branched $C_{1-18}$ alkylene chain, wherein 0-9 methylene units of Q are independently replaced by —Cy—, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
- —Cy— is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the x group is about 10 to about 250. In certain embodiments, the x group is about 25. In other embodiments x is about 10 to about 50. In other embodiments, x is about 50. According to yet another embodiment, x is about 75. In other embodiments, x is about 100. In certain embodiments, x is about 40 to about 80. In other embodiments, x is selected from 10±5, 15±5, 25±5, 50±5, 75±10, 100±10, or 125±10.

In certain embodiments, the Q group is a chemical moiety representing an oligomer of ethylene amine, —(NH$_2$—CH$_2$—CH$_2$)—. In some embodiments, Q is a bivalent, saturated or unsaturated, straight or branched C$_{1-20}$ alkylene chain, wherein 0-9 methylene units of Q are independently replaced by —NH—, —C(O)—, —NHC(O)—, or —C(O)NH—. In certain embodiments, Q is a branched alkylene chain wherein one or more methine carbons is replaced with a nitrogen atom to form a trivalent amine group. Specific examples of Q groups can be found in Table 1a, Table 1b, and Table 1c.

TABLE 1a

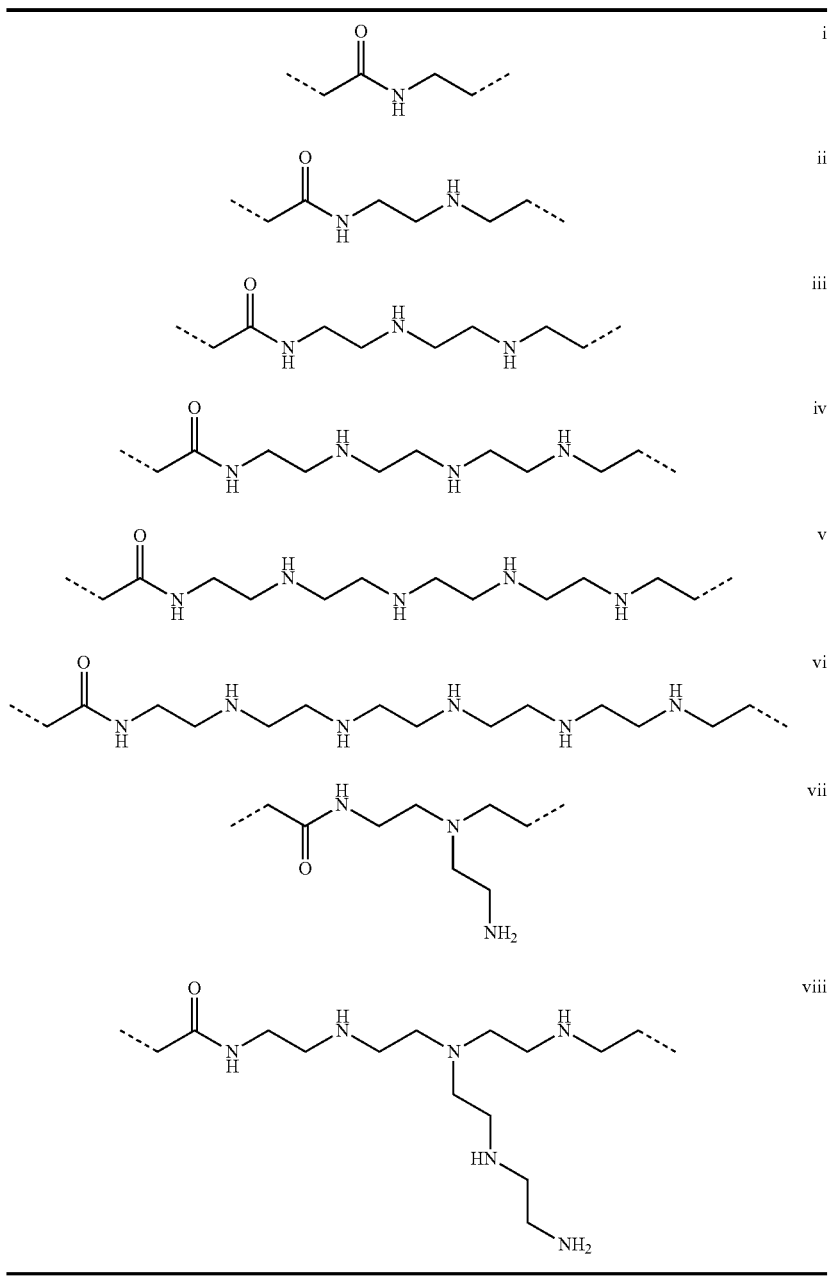

TABLE 1b

| | |
|---|---|
| ![structure] | ix |
| ![structure] | x |
| ![structure] | xi |
| ![structure] | xii |
| ![structure] | xiii |
| ![structure] | xiv |
| ![structure] | xv |
| ![structure] | xvi |

TABLE 1c

| | |
|---|---|
| ![structure] | xvii |
| ![structure] | xviii |
| ![structure] | xix |

TABLE 1c-continued

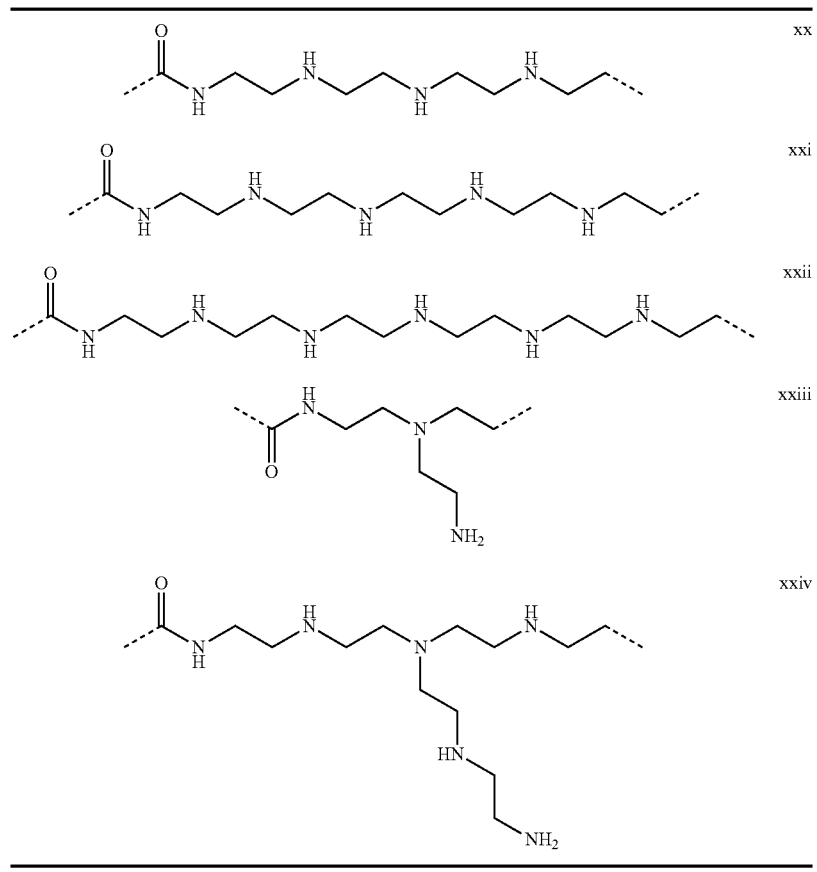

One skilled in the art will recognize that the stereochemistry of the poly(amino acid) represented in Formula I is undefined. It is understood that this depiction can represent an all L conformation, an all D conformation, or any random mixture of D and L isomers.

In certain embodiments, the cationic polymer described above contains a mixture of primary and secondary amine groups on the side chain of the poly(amino acid). One of ordinary skill in the art will recognize that primary amine groups interact with phosphates in the polynucleotide to form the polyplex, whereas secondary amine groups function as a buffering group, or proton sponge, which aids in endosomal escape via endosome disruption. Ideally, one would select the optimum number of primary and secondary amines to both complex the polynucleotide and allow for sufficient endosomal escape, while limiting cytotoxicity.

One skilled in the art will recognize that the "100" of Formula I and the x group of Formula II represent a average number of "repeats" or monomer segments which comprise the polymer. This number is often called the degree of polymerization (DP). Because this number represents an average, it is understood that this number will vary from polymer to polymer. Furthermore, this number may vary by up to 10% from batch to batch. One skilled in the art will also recognize that the polydispersity index (PDI) represents the nature of the distribution around the degree of polymerization. A PDI of 1.0 indicates that all polymers are comprised of the exact same DP (e.g. a protein) while a PDI of 2.0 represents a Gaussian distribution.

B. Polynucleotide Encapsulation

The present invention provides the preparation of a polyplex formed by the addition of a cationic polymer and a polynucleotide.

In water, such cationic copolymers co-assemble with polynucleotides through electrostatic interactions between the cationic side chains of the polymer and the anionic phosphates of the polynucleotide to form a polyplex. In some cases, the number of phosphates on the polynucleotides may exceed the number of cationic charges on the multiblock copolymer. It will be appreciated that multiple polymers may be used to achieve charge neutrality (i.e. N/P=1) between the polymer and encapsulated polynucleotide. It will also be appreciated that when an excess of polymer is used to encapsulate a polynucleotide, the polymer/polynucleotide complex can possess an overall positive charge (i.e. N/P>1).

As described herein, polyplexes of the present invention can be prepared with any polynucleotide agent. In one embodiment, the encapsulated polynucleotide is a plasmid DNA (pDNA). As used herein, pDNA is defined as a circular, double-stranded DNA that contains a DNA sequence (cDNA or complementary DNA) that is to be expressed in cells either in culture or in vivo. The size of pDNA can range from 3 kilo base pairs (kb) to greater than 50kb. The cDNA that is contained within plasmid DNA is usually between 1-5 kb in length, but may be greater if larger genes are incorporated. pDNA may also incorporate other sequences that allow it to be properly and efficiently expressed in mammalian cells, as well as replicated in bacterial cells. In certain embodiments, the encapsulated pDNA expresses a therapeutic gene in cell culture, animals, or humans that possess a defective or missing gene that is responsible for and/or correlated with disease.

In certain embodiments, an encapsulated polynucleotide is capable of silencing gene expression via RNA interference (RNAi). As defined herein, RNAi is a cellular mechanism that suppresses gene expression during translation and/or hinders the transcription of genes through destruction of messenger RNA (mRNA). Without wishing to be bound by any particular theory, it is believed that endogenous double-stranded RNA located in the cell are processed into 20-25 nt short-interfering RNA (siRNA) by the enzyme Dicer. siRNA subsequently binds to the RISC complex (RNA-induced silencing nuclease complex), and the guide strand of the siRNA anneals to the target mRNA. The nuclease activity of the RISC complex then cleaves the mRNA, which is subsequently degraded (*Nat. Rev. Mol. Cell Biol.*, 2007, 8, 23).

In one embodiment, an encapsulated polynucleotide is a siRNA. As used herein, siRNA is defined as a linear, double-stranded RNA that is 20-25 nucleotides (nt) in length and possesses a 2 nt, 3' overhang on each end which can induce gene knockdown in cell culture or in vivo via RNAi. In certain embodiments, the encapsulated siRNA suppresses disease-relevant gene expression in cell culture, animals, or humans.

In certain embodiments, the encapsulated polynucleotide is pDNA that expresses a short-hairpin RNA (shRNA). As used herein, shRNA is a linear, double-stranded RNA, possessing a tight hairpin turn, which is synthesized in cells through transfection and expression of a exogenous pDNA. Without wishing to be bound by any particular theory, it is believed that the shRNA hairpin structure is cleaved to produce siRNA, which mediates gene silencing via RNA interference. In certain embodiments, the encapsulated shRNA suppresses gene expression in cell culture, animals, or humans that are responsible for a disease via RNAi.

In certain embodiments, the encapsulated polynucleotide is a microRNA (miRNA). As used herein, miRNA is a linear, single-stranded RNA that ranges between 21-23 nt in length and regulates gene expression via RNAi (Cell, 2004, 116, 281). In certain embodiments, an encapsulated miRNA suppresses gene expression in cell culture, animals, or humans that are responsible for a disease via RNAi.

In another embodiment, an encapsulated polynucleotide is a messenger RNA (mRNA). As used herein, mRNA is defined as a linear, single stranded RNA molecule, which is responsible for translation of genes (from DNA) into proteins. In certain embodiments, the encapsulated mRNA is encoded from a plasmid cDNA to serve as the template for protein translation. In certain embodiments, an encapsulated mRNA translates therapeutic proteins, in vitro and/or in vivo, which can treat disease.

In certain embodiments, an encapsulated polynucleotide is an antisense RNA (asRNA). As used herein, asRNA is a linear, single-stranded RNA that is complementary to a targeted mRNA located in a cell. Without wishing to be bound by any particular theory, it is believed that asRNA inhibits translation of a complementary mRNA by pairing with it and obstructing the cellular translation machinery. It is believed that the mechanism of action for asRNA is different from RNAi because the paired mRNA is not destroyed. In certain embodiments, an encapsulated asRNA suppresses gene expression in cell culture, animals, or humans that are responsible for a disease by binding mRNA and physically obstructing translation.

In certain embodiments, the present invention provides a polyplex having a polynucleotide encapsulated therein, comprising a cationic polymer of formula I or a salt thereof:

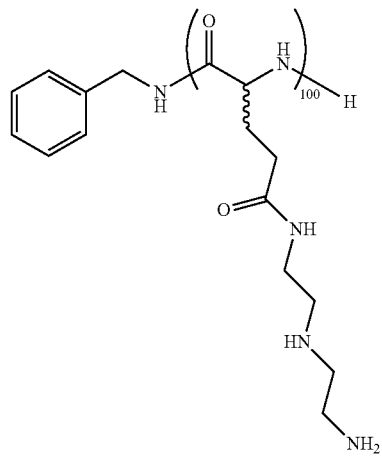

I

In certain embodiments, the present invention provides a polyplex having a polynucleotide encapsulated therein, comprising a cationic polymer of formula II:

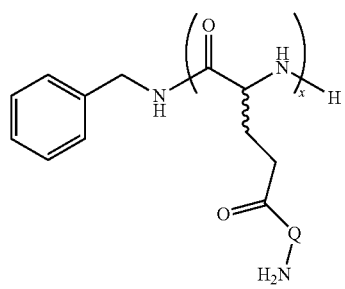

II wherein each of x and Q and as described in classes and subclasses herein, both singly and in combination.

In certain embodiments, the polynucleotide complexation is performed at neutral pH. In other embodiments, the polynucleotide complexation is performed at pH of 4-8. In other embodiments, the polynucleotide complexation is performed at pH of about 7.4. In other embodiments, the polynucleotide complexation is performed at pH of 6.5-7.5.

Surprisingly, it was found that preparing the complexes in the presence of bovine serum albumin (BSA) significantly increased transfection efficiency. Percentages of BSA in the aqueous buffer was screened from 1% to 10%, with 5% being optimal for transfection efficiency. Additionally, it was found that the salt in this BSA solution also effected transfection efficiency. TRIS, HEPES, and borate buffers were screened, with a mixture of borate and TRIS giving optimal results. The concentration of the buffer, as well as the pH of the borate buffer was also screened, with 50 mM at pH 8.5 being optimal for transfection efficiency.

In certain embodiments of the present invention, the polyplex formation is performed in the presence of bovine serum albumin, with or without the presence of salts, including but not limited to TRIS [tris(hydroxymethyl)aminomethane)], borate ($BO_3^{3-}$), or HEPES [4-(2-hydroxyethyl)-1-piperazineethanesulfonic acid].

In one embodiment, the present invention provides a method for transfecting cells, comprising the following steps:
1) dissolution of a polymer of Formula I in either water or 5% bovine serum albumin (BSA) in 50 mM borate at pH 8.5
2) addition of a polynucleotide solution to the polymer solution of step 1 followed by mixing at room temperature 3) addition of one of the following solutions: water; 5% BSA in 50 mM borate at pH 8.3; or 5% BSA in 10 mM Tris at pH 8 to the solution formed in step 2
4) mixing of the resulting solution of step 3 and incubation at room temperature
5) addition of the mixed solution of step 4 to live cells followed by incubation.

In one embodiment, the present invention provides a method for transfecting cells, comprising the following steps:
1) dissolution of a polymer of Formula II in either water or 5% bovine serum albumin (BSA) in 50 mM borate at pH 8.5
2) addition of a polynucleotide solution to the polymer solution of step 1 followed by mixing at room temperature
3) addition of one of the following solutions: water; 5% BSA in 50 mM borate at pH 8.3; or 5% BSA in 10 mM Tris at pH 8 to the solution formed in step 2
4) mixing of the resulting solution of step 3 and incubation at room temperature
5) addition of the mixed solution of step 4 to live cells followed by incubation.

In one embodiment, the present invention provides a method for transfecting cells, comprising the following steps:
1) dissolution of a polymer of Formula I in 5% bovine serum albumin in 50 mM borate at pH 8.5
2) addition of a polynucleotide solution to the polymer solution of step 1 followed by mixing at room temperature
3) addition of 5% BSA in 50 mM borate at pH 8.5 to the solution formed in step 2
4) mixing of the resulting solution of step 3 and incubation at room temperature
5) addition of the mixed solution of step 4 to live cells followed by incubation.

In one embodiment, the present invention provides a method for transfecting cells, comprising the following steps:
1) dissolution of a polymer of Formula I in 5% bovine serum albumin in 50 mM borate and 10 mM TRIS at pH 8.5,
2) dilution of a polynucleotide solution with 5% bovine serum albumin in 50 mM borate and 10 mM TRIS at pH 8.5,
3) combining the solutions prepared in step 1 and step 2,
4) mixing of the resulting solution of step 3 and incubation at room temperature,
5) addition of the mixed solution of step 4 to live cells followed by incubation.

In one embodiment, the present invention provides a method for transfecting cells, comprising the following steps:
1) dissolution of a polymer of Formula I in 5% bovine serum albumin in 50 mM borate at pH 8.5,
2) dilution of a polynucleotide solution with 5% bovine serum albumin in 50 mM borate at pH 8.5,
3) combining the solutions prepared in step 1 and step 2,
4) addition of one of the following solutions: 5% bovine serum albumin in 10 mM Tris at pH 8.5 to the solution formed in step 3
5) mixing of the resulting solution of step 4 and incubation at room temperature
6) addition of the mixed solution of step 5 to live cells followed by incubation.

In one embodiment, the present invention provides a method for transfecting cells, comprising the following steps:
1) dissolution of a polymer of Formula I in 5% bovine serum albumin in 10 mM TRIS at pH 8.5,
2) dilution of a polynucleotide solution with 5% bovine serum albumin in 10 mM TRIS at pH 8.5,
3) combining the solutions prepared in step 1 and step 2,
4) mixing of the resulting solution of step 3 and incubation at room temperature,
5) addition of the mixed solution of step 4 to live cells followed by incubation.

In one embodiment, the present invention provides a method for transfecting cells, comprising the following steps. Poly(Glu-DET) polymers are diluted to N:P 10 ratio (20 μL of N:P 50 stock solution) in either: [A) H2O (80 μL), B) 5% BSA-50 mM Borate pH 8.3 (80 μL), C) H2O (80 μL) or D) 5% BSA-50 mM Borate pH 8.3 (80 μL)], for a final volume of 100 μL. Twenty μg of plasmid DNA is diluted separately in each of the above solutions (for a final 100 μL total volume). Polymer solutions are then added to their corresponding DNA solutions, mixed and incubated for 15 min at room temperature (for 200 μL total, A, B, C and D). To each complexed solution, 300 μL of either: [A) H2O, B) 5% BSA-50 mM Borate pH 8.3, C) 5% BSA-10 mM Tris pH 8 or D) 5% BSA-10 mM Tris pH 8] was added, mixed by pipetting and incubated for 15 min at room temperature (for a final 500 μL total volume). Six and a quarter μL of the transfection reagent was added to each well of a 96 well plate (0.25 μg DNA/well), and cells were incubate overnight at 37° C.

4. Uses, Methods, and Compositions

In order that the invention described herein may be more fully understood, the following examples are set forth. It will be understood that these examples are for illustrative purposes only and are not to be construed as limiting this invention in any manner.

EXAMPLES

Example 1

Formulation of Polymer/Nucleic Acid Polyplexes for Transfection

Poly(D/L Glu-DET)/DNA transfection complexes were prepared by initially adding equal volumes of Poly(D/L Glu-DET) solution (100 μL dissolved in either dH$_2$O or 5% BSA-50 mM Borate pH 8.3) and plasmid DNA solution (20 μg dissolved in 100 μL in either dH$_2$O or 5% BSA-50 mM Borate pH 8.3) at N:P ratio 10. Polymer was added to DNA solution, for a final volume of 200 μL, and incubated at room temperature for at least 15 min to allow polyplex formation. Transfection polyplexes were formed by incubating 200 μL of Poly(D/L Asp-DET)/DNA N:P 10 polyplexes with 300 μL of either H$_2$O, 5% BSA-50 mM Borate pH 8.3, or 5% BSA-10 mM Tris pH 8 for 15 min at room temperature to give a final volume of 500 μL for all samples. (See FIG. 1 for schematic).

Example 2

Gel Retardation of DNA Complexed with D/L Glu-DET in Different Buffer Conditions Polyplexes containing GFP plasmid DNA (pZs Green; Promega, Madison, WI) were prepared (as described in Example 1) at an N:P ratio of 10. Twelve and a half μL of each formulation (0.5 μg DNA) was run on a 1% agarose gel and visualized by ethidium bromide staining, FIG. 2. DNA retardation was observed in all polyplex samples. Heparin was added to duplicate samples to dissociate DNA from polymers. All heparin treated samples contained intact DNA.

Example 3

GFP Expression of Cancer Cells Transiently Transfected with Poly(D/L Glu-DET) Polymers in Various Buffered Solutions HCT-116, LNCaP and 293 cancer cells were also transfected in triplicate in 96-well plates with Poly(D/L Glu-DET)/DNA polyplexes (Example 1), containing GFP expressing plasmid DNA pZs-Green, N:P 10 ratio at a final DNA concentration of 0.25 μg per well, FIG. 3. Twenty-four hr after transfection, cells were imaged using phase contrast (inset) and fluorescence for GFP expression (bottom panel), ×10. Transfection polyplexes showed high levels of GFP expression for all cell lines examined, FIG. 3. Cells transfected with the various polyplexes showed little cytotoxicity, FIG. 4.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:

1. A method for transfecting cells, comprising the following steps:
   1) dissolution of a polymer of Formula I in 5% bovine serum albumin in 50 mM borate and 10 mM TRIS at pH 8.5,
   2) dilution of a polynucleotide solution with 5% bovine serum albumin in 50 mM borate and 10 mM TRIS at pH 8.5,
   3) combining the solutions prepared in step 1 and step 2,
   4) mixing of the resulting solution of step 3 and incubation at room temperature,
   5) addition of the mixed solution of step 4 to live cells followed by incubation;
   wherein Formula I is

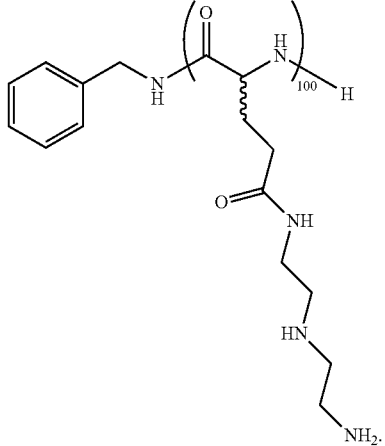

2. A method for transfecting cells, comprising the following steps:
   1) dissolution of a polymer of Formula I in 5% bovine serum albumin in 50 mM borate at pH 8.5,
   2) dilution of a polynucleotide solution with 5% bovine serum albumin in 50 mM borate at pH 8.5,
   3) combining the solutions prepared in step 1 and step 2,
   4) addition of one of the following solutions: 5% bovine serum albumin in 10 mM Tris at pH 8.5 to the solution formed in step 3
   5) mixing of the resulting solution of step 4 and incubation at room temperature
   6) addition of the mixed solution of step 5 to live cells followed by incubation;
   wherein Formula I is

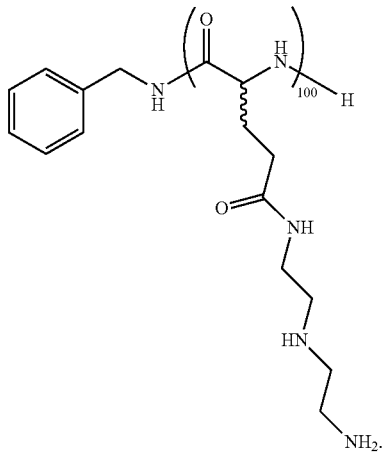

* * * * *